(12) United States Patent  
Gadol et al.

(10) Patent No.: US 12,290,375 B2
(45) Date of Patent: May 6, 2025

(54) PREDICTING AGING TREATMENT OUTCOMES BASED ON A SKIN AGEOTYPE

(71) Applicant: L'Oreal, Paris (FR)

(72) Inventors: Sandrine Gadol, New York, NY (US); Michelle Rathman-Josserand, La Celle Saint-Cloud (FR); Benjamin Askenazi, Clichy (FR); Panagiotis-Alexandros Bokaris, Paris (FR); Nukhet Cavusoglu, Claye-Souilly (FR); Stephanie Nouveau, Boulogne-Billancourt (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/783,617

(22) PCT Filed: Apr. 29, 2022

(86) PCT No.: PCT/US2022/027108
§ 371 (c)(1),
(2) Date: Jun. 8, 2022

(87) PCT Pub. No.: WO2022/232627
PCT Pub. Date: Nov. 3, 2022

(65) Prior Publication Data
US 2024/0298960 A1 Sep. 12, 2024

Related U.S. Application Data

(60) Provisional application No. 63/182,673, filed on Apr. 30, 2021.

(30) Foreign Application Priority Data

Jul. 23, 2021 (FR) ........................... 2108019

(51) Int. Cl.
*A61B 5/00* (2006.01)
*A45D 44/00* (2006.01)
(Continued)

(52) U.S. Cl.
CPC ............ *A61B 5/442* (2013.01); *A45D 44/005* (2013.01); *A61B 5/0077* (2013.01); *A61B 5/445* (2013.01);
(Continued)

(58) Field of Classification Search
None
See application file for complete search history.

(56) References Cited

U.S. PATENT DOCUMENTS 9,842,358 B1 12/2017 Butler et al.
9,955,909 B2 5/2018 L'Oreal
(Continued)

FOREIGN PATENT DOCUMENTS

JP 2017502732 A 1/2017
JP 2020522810 A 7/2020
(Continued)

OTHER PUBLICATIONS

Office Action mailed Sep. 2, 2024, in corresponding Japanese application No. 2023-562574, filed Apr. 29, 2022, 10 pages.
(Continued)

*Primary Examiner* — Andrew H Lam
(74) *Attorney, Agent, or Firm* — Christensen O'Connor Johnson Kindness PLLC

(57) ABSTRACT

In some embodiments, a method of determining a personalized skincare recommendation is provided. A computing system receives data depicting a face of a subject. The computing system determines features based on the data depicting the face of the subject. The computing system provides the features to an ageotype classifier to generate a
(Continued)

predicted skin ageotype for the subject. The computing system generates the personalized skincare recommendation based on at least the predicted skin ageotype.

18 Claims, 9 Drawing Sheets

(51) Int. Cl.
 *G06V 40/16* (2022.01)
 *G16H 10/60* (2018.01)

(52) U.S. Cl.
 CPC .......... *A61B 5/7264* (2013.01); *A61B 5/7275* (2013.01); *G06V 40/171* (2022.01); *G16H 10/60* (2018.01); *A45D 2044/007* (2013.01)

(56) References Cited

U.S. PATENT DOCUMENTS

| | | | |
|---|---|---|---|
| 2016/0154992 A1 | 6/2016 | Shinoda et al. | |
| 2017/0020436 A1* | 1/2017 | Flament | A61B 5/0077 |
| 2018/0350071 A1* | 12/2018 | Purwar | G06N 3/08 |
| 2019/0213453 A1 | 7/2019 | Ludwinski et al. | |
| 2020/0066405 A1 | 2/2020 | Peyman | |
| 2020/0170564 A1 | 6/2020 | Jiang et al. | |
| 2020/0342213 A1 | 10/2020 | Dissanayake et al. | |
| 2021/0027897 A1 | 1/2021 | Rasochova et al. | |
| 2021/0209427 A1 | 7/2021 | Ludwinski et al. | |

FOREIGN PATENT DOCUMENTS

| | | |
|---|---|---|
| JP | 2020525491 A | 8/2020 |
| JP | 2020531027 A | 11/2020 |
| JP | 2021510217 A | 4/2021 |
| WO | 2020/169214 A1 | 8/2020 |

OTHER PUBLICATIONS

French Written Opinion and Search Report mailed Apr. 5, 2022, issued in corresponding French Application No. FR2108019, filed Jul. 23, 2021, 6 pages.

International Search Report and Written Opinion mailed Jul. 29, 2022, issued in corresponding International Application No. PCT/US2022/027108, filed Apr. 29, 2022, 13 pages.

* cited by examiner

PREDICTING AGING TREATMENT OUTCOMES BASED ON A SKIN AGEOTYPE

CROSS REFERENCE TO RELATED APPLICATIONS

This application is a National Stage of International Application No. PCT/US2022/027108, filed Apr. 29, 2022, which claims the benefit of Provisional Application No. 63/182,673, filed Apr. 30, 2021. This application also claims priority to French Application No. 2108019, filed Jul. 23, 2021. The entire disclosures of these applications are hereby incorporated by reference herein for all purposes.

DESCRIPTION OF THE DRAWINGS

Many of the attendant advantages of this invention will become more readily appreciated as the same become better understood by reference to the following detailed description, when taken in conjunction with the accompanying drawings, wherein.

DETAILED DESCRIPTION

Figure 1:
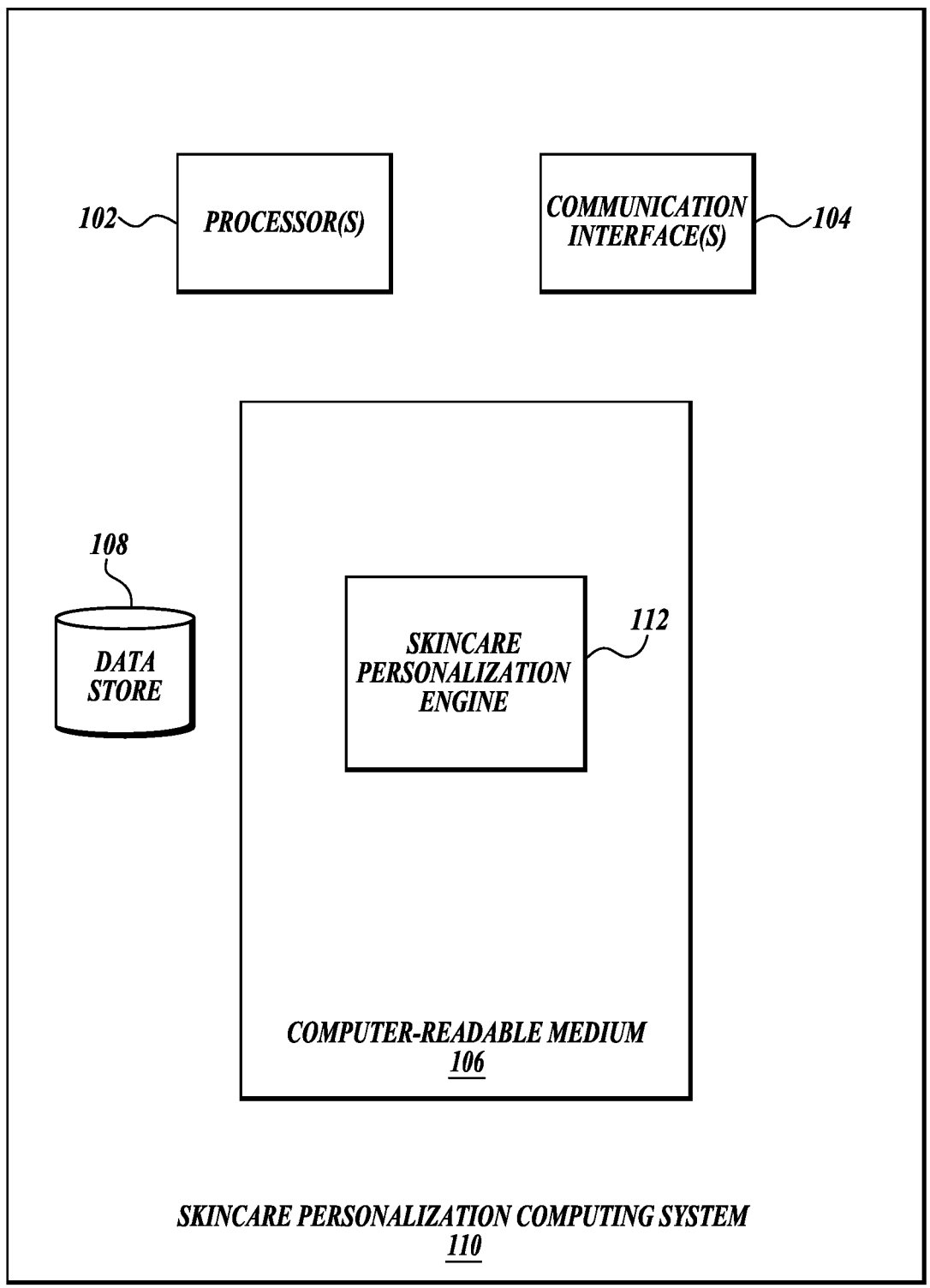
FIG. 1 is a block diagram that illustrates aspects of a non-limiting example embodiment of a skincare personalization computing system according to various aspects of the present disclosure.

In some embodiments of the present disclosure, systems, methods, and devices are provided that provide improved recommendations for skincare regimes according to ageotype of a subject. It has been determined that there are multiple types of aging that the human body experiences over time: metabolic, immunological, liver dysfunction, and kidney disfunction. The presence or absence of these types of aging can be used to organize subjects into one or more ageotypes. Ageotypes to which the subject belongs, including but not limited to skin ageotypes, help predict what clinical signs of aging the subject will experience. For example, subjects in an inflammation skin ageotype, a dehydration skin ageotype, or a glycation skin ageotype may each experience different clinical signs of aging.

The present disclosure allows skincare treatments to be recommended to reduce the incidence and/or severity of clinical signs of aging based on the determined skin ageotype of the subject. Using these recommended skincare treatments, skin health and clinical signs of aging can be managed more effectively. In some embodiments of the present disclosure, the skin ageotype and/or clinical signs of aging likely to be experienced by the subject are determined based on data such as imagery captured of the subject.

In some embodiments, an analysis of facial structure, facial expressions, skin tone/phenotype, and available biological data determines in which skin ageotype a subject belongs. If one skin ageotype presenting similarities is, for instance, called the inflammaging group, this group may be sub-categorized by age, location, lifestyle, etc. The analysis of the inflammaging sub groups overall may be used to derive a general inflammaging aging trajectory path (e.g., specific clinical signs of aging present in the group including but not limited to sagging, spots, etc), which can be contrasted by analysis of the sub-groups (same age, different location/same age, different lifestyle, etc.) to be able to establish risk factors of the groups. For instance, the inflammaging skin ageotype may be determined to be even more prone to sagging when having a rich diet and exposed to a lot of sun.

The analysis of one subject's data from the inflammaging group may be compared with the inflammaging group (and augmented by subepidermal imaging when available) to determine a physiological age and highlight areas to correct/improve (e.g., areas lagging behind the same inflammaging sub group of age/location/lifestyle/etc) and the areas to capitalize on (e.g., areas to maintain or augment). This will establish a personalized skin age management strategy including ingredients and product recommendations for improvement. For example, the system may provide a recommendation such as, "The subject should capitalize on their firm, wrinkle free skin by focusing on high SPF, AOX, and a diet rich in fatty acids to reduce and prevent inflammation, to maintain a wrinkle-free skin and restore glow."

Based on additional biological analysis, when available, the individual skin management and product recommendation may include a precision recommendation of which relevant set of active ingredients the subject will respond to. This helps ensure that the performance of the treatment is optimized for the specific individual (responder/non-responder concept). For example, the system may provide a recommendation such as, "To keep a wrinkle-free skin surface and restore a youthful glow, biological test results show a response to retinol and not vitamin C. Accordingly, we recommend a retinol serum with SPF."

In some embodiments, an app or other online tool may allow the subject to take pictures and track the aging score to get more personalized advice, adjust their skin routine to their need based on progress and evolution of risk factors/exposome in order to be proactive to prevent inflammaging and get visible results.

The techniques disclosed herein provide a variety of technical improvements. As one non-limiting example, the collection of images and/or video of a face in response to prompts that guide a subject through a predetermined set of one or more expressions improves the quality of the data collected and improves the usefulness of the data in automatically predicting a skin ageotype for the subject, as well as increasing the efficiency of collecting the high-quality, useful data. As another non-limiting example, collecting other data that may be provided to a skin ageotype classifier along with the images and/or video of a face (including but not limited to exposome information and primary spoken language information) helps to further improve the accuracy of the automatic skin ageotype determination. Further, automatic and accurate prediction of a skin ageotype helps to improve the quality of automatically generated personalized skincare recommendations, thereby improving the quality of both the generation of the recommendation itself and the effectiveness of the treatment of the skin of the subject.

FIG. 1 is a block diagram that illustrates aspects of a non-limiting example embodiment of a skincare personalization computing system according to various aspects of the present disclosure. The illustrated skincare personalization computing system 110 may be implemented by any computing device or collection of computing devices, including but not limited to a desktop computing device, a laptop computing device, a mobile computing device, a server computing device, a computing device of a cloud computing system, and/or combinations thereof.

As shown, the skincare personalization computing system 110 includes one or more processors 102, one or more communication interfaces 104, a data store 108, and a computer-readable medium 106.

In some embodiments, the processors 102 may include any suitable type of general-purpose computer processor. In some embodiments, the processors 102 may include one or more special-purpose computer processors or AI accelerators optimized for specific computing tasks, including but not limited to graphical processing units (GPUs), vision processing units (VPTs), and tensor processing units (TPUs).

In some embodiments, the communication interfaces 104 include one or more hardware and or software interfaces suitable for providing communication links between components. The communication interfaces 104 may support one or more wired communication technologies (including but not limited to Ethernet, FireWire, and USB), one or more wireless communication technologies (including but not limited to Wi-Fi, WiMAX, Bluetooth, 2G, 3G, 4G, 5G, and LTE), and/or combinations thereof.

As shown, the computer-readable medium 106 has stored thereon logic that, in response to execution by the one or more processors 102, cause the skincare personalization computing system 110 to provide a skincare personalization engine 112.

As used herein, "computer-readable medium" refers to a removable or nonremovable device that implements any technology capable of storing information in a volatile or non-volatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

In some embodiments, the skincare personalization engine 112 is configured to determine features based on data depicting a face of a subject, and to determine a skin ageotype of the subject based on the features. The skincare personalization engine 112 may use one or more classifiers to determine the skin ageotype of the subject, and may be configured to train such classifiers based on ground truth data and associated data for previous subjects. The skincare personalization engine 112 may also be configured to determine skincare recommendations based on the determined skin ageotype. The skincare personalization engine 112 may use the data store 108 to store the features, the recommendations, and/or the classifiers.

Further description of the configuration of each of these components is provided below.

As used herein, "engine" refers to logic embodied in hardware or software instructions, which can be written in one or more programming languages, including but not limited to C, C++, C#, COBOL, JAVA™, PHP, Perl, HTML, CSS, Javascript, VBScript, ASPX, Go, and Python. An engine may be compiled into executable programs or written in interpreted programming languages. Software engines may be callable from other engines or from themselves. Generally, the engines described herein refer to logical modules that can be merged with other engines, or can be divided into sub-engines. The engines can be implemented by logic stored in any type of computer-readable medium or computer storage device and be stored on and executed by one or more general purpose computers, thus creating a special purpose computer configured to provide the engine or the functionality thereof. The engines can be implemented by logic programmed into an application-specific integrated circuit (ASIC), a field-programmable gate array (FPGA), or another hardware device.

As used herein, "data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Another non-limiting example embodiment of a system of the present disclosure comprises an ageotype unit and a recommendation unit. The ageotype unit includes computational circuitry configured to predict an onset of an aging event (e.g., wrinkles, sagginess, etc.) based on facial movement, facial structures, and the like to generate skin ageotype classifiers. The recommendation unit includes computational circuitry configured to generate a personalized skincare recommendation responsive to one or more ageotype classifiers.

Yet another non-limiting example embodiment of a system of the present disclosure comprises an ageotype unit and an outcomes unit. The ageotype unit includes computational circuitry configured to generate a skin ageotype indicative of an onset of an aging event (e.g., wrinkles, sagginess, etc.) based on facial movement, facial structures, and the like. The outcomes unit includes computational circuitry configured to generate a predicted effectiveness rating for a skincare recommendation responsive to one or more skin ageotype inputs.

Figure 2:
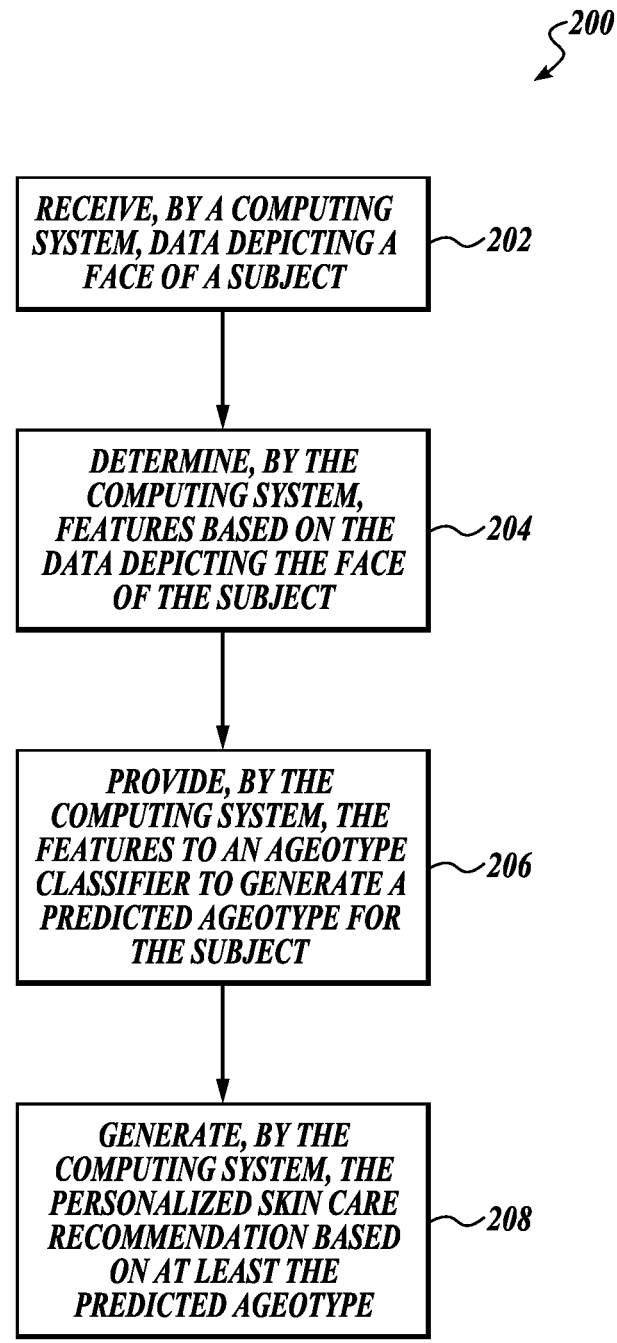
FIG. 2 illustrates a method 200 in accordance with a non-limiting example embodiment of the present disclosure.
Figure 3A:
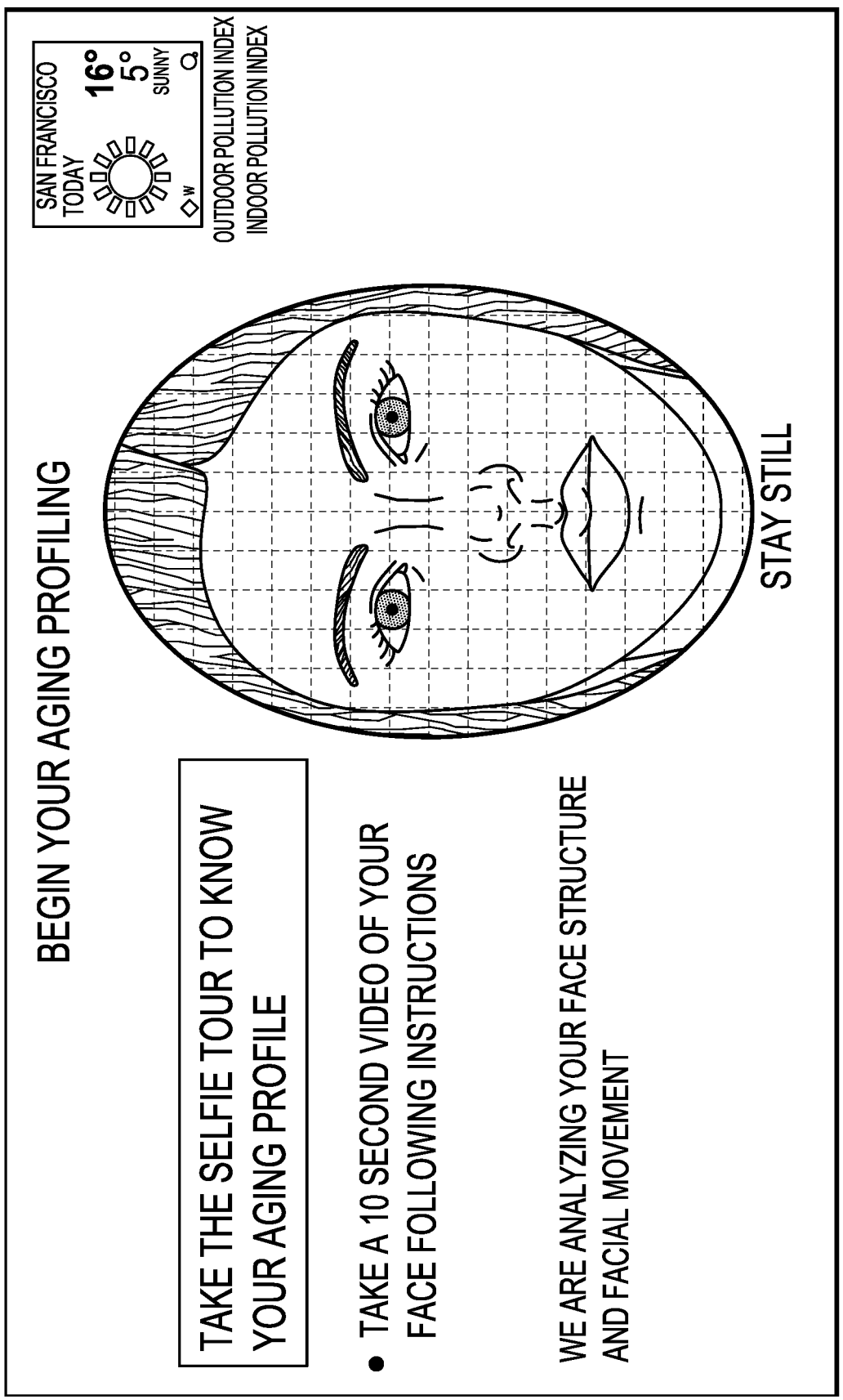
FIG. 3A-FIG. 3E illustrate non-limiting example embodiments of prompts presented according to various aspects of the present disclosure.
Figure 3B:
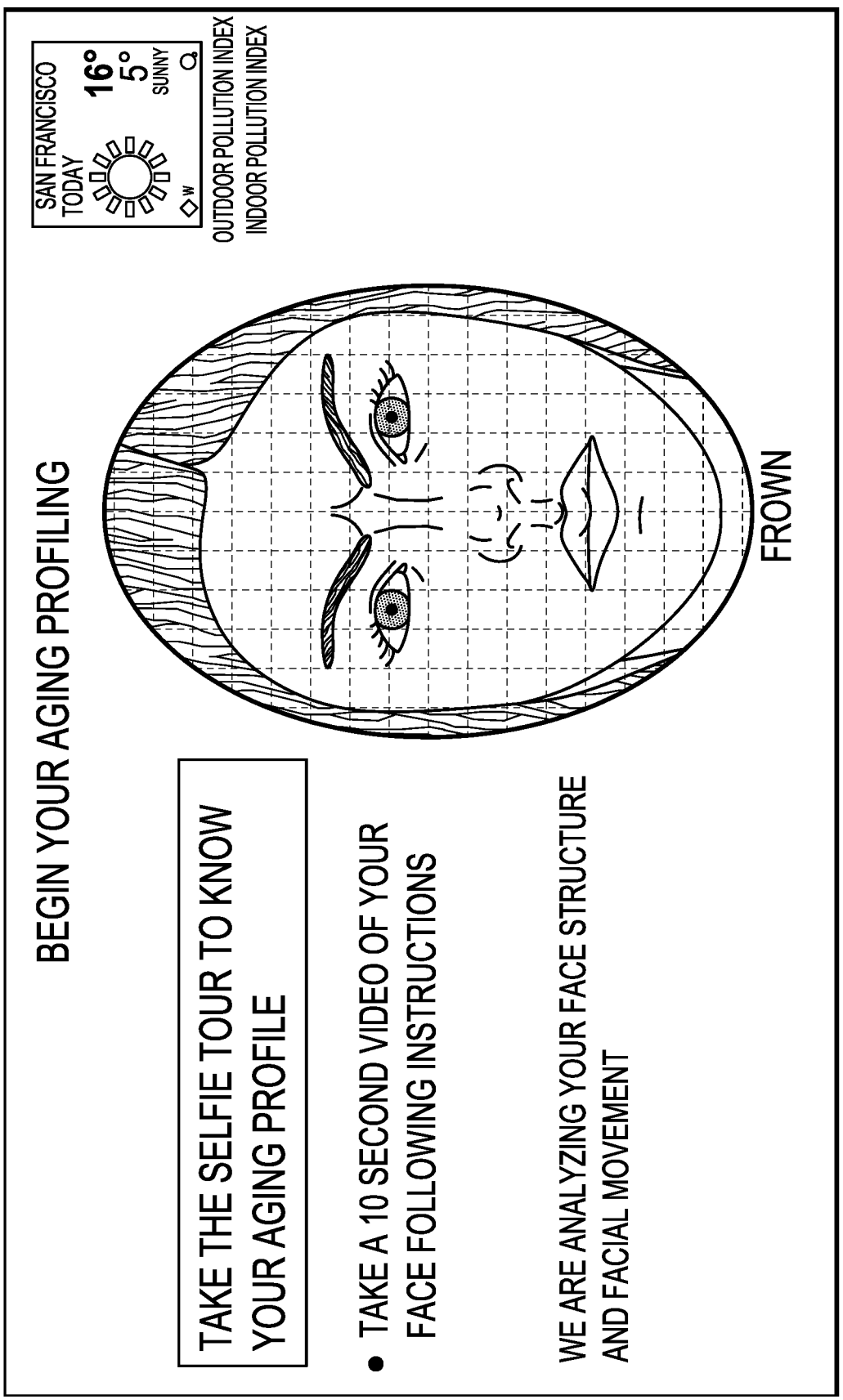
Figure 3C:
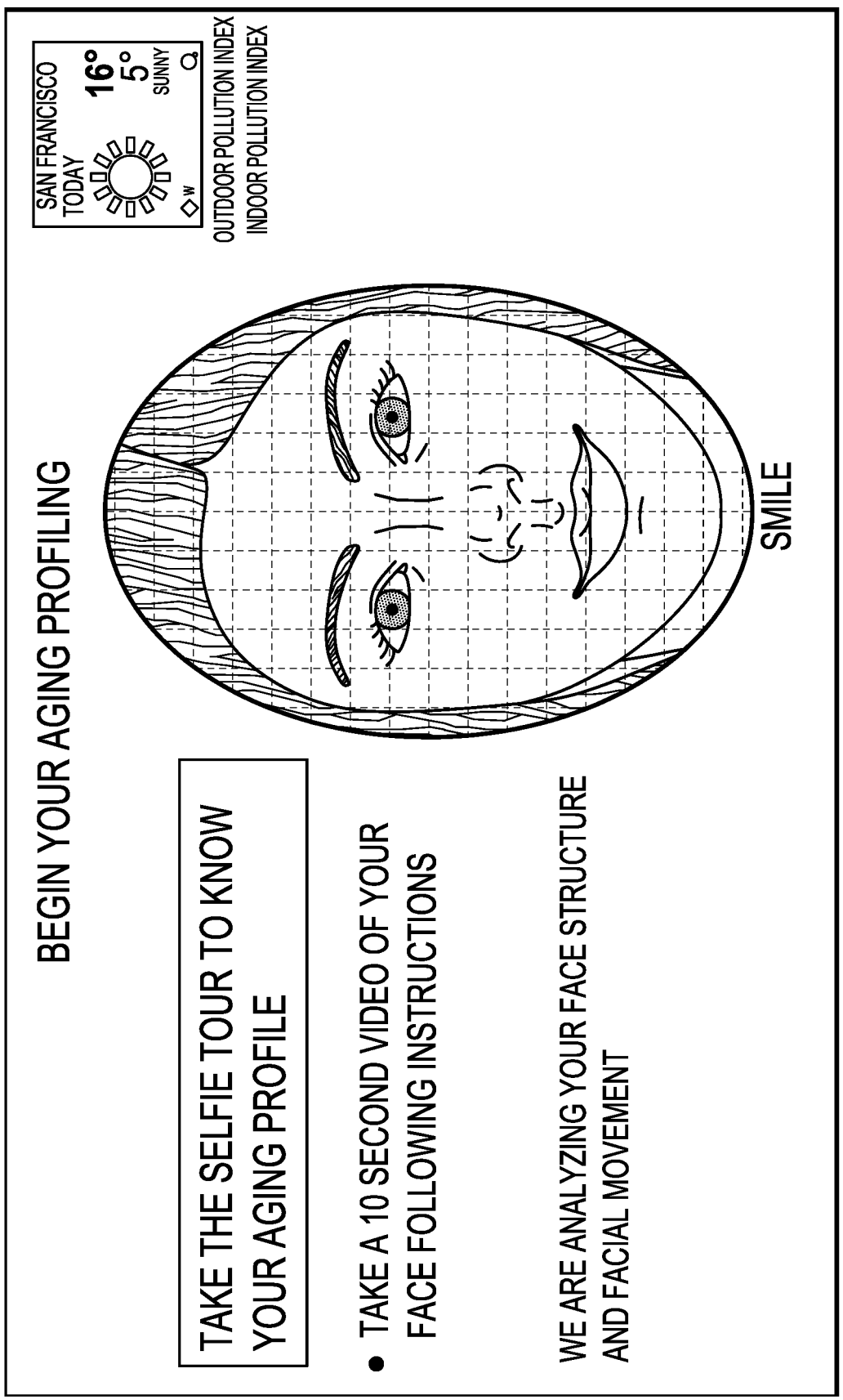
Figure 3D:
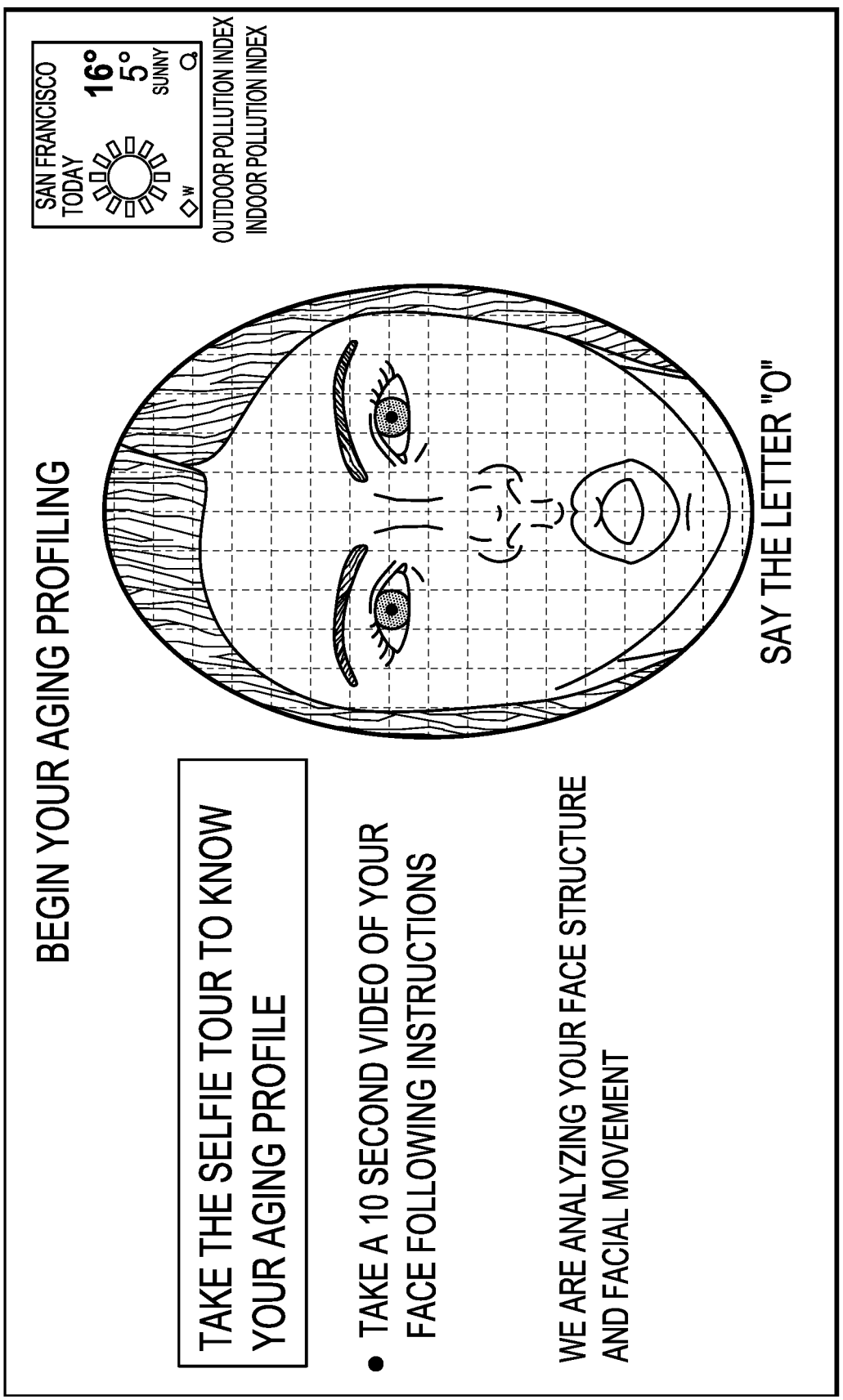
Figure 3E:
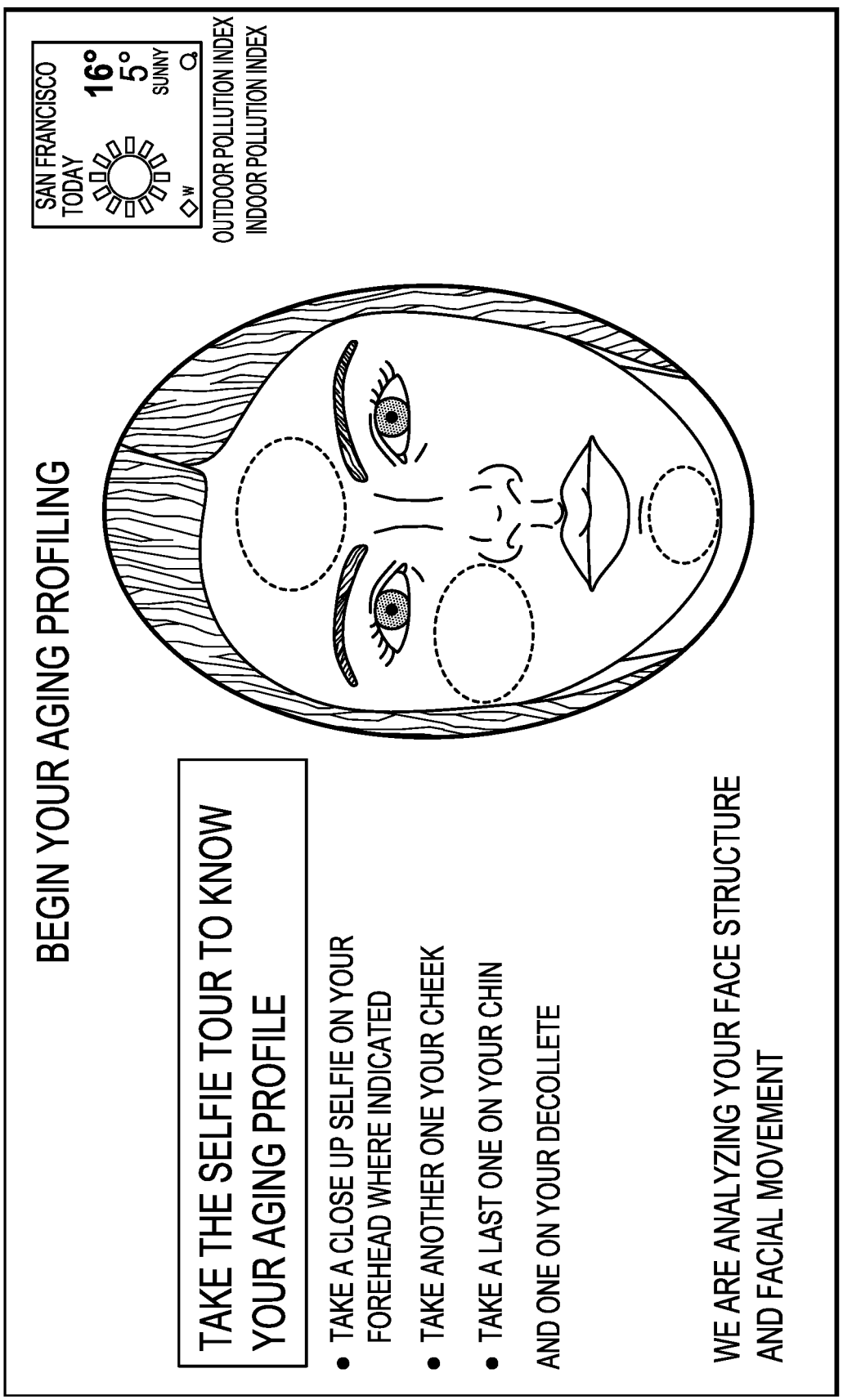

FIG. 2 is a flowchart illustrating a non-limiting example embodiment of a method of determining a personalized skincare recommendation according to various aspects of the present disclosure.

At block 202, a computing system (such as skincare personalization computing system 110) receives data depicting a face of a subject. The data depicting the face of the subject may be gathered using any suitable technique. In some embodiments, the data depicting the face of the subject may include one or more images of the face of the subject captured by a digital camera, including but not limited to a selfie image captured by a smartphone. In some embodiments, the data depicting the face of the subject may include one or more videos of the face captured by a digital video camera, including but not limited to a selfie video captured by a smartphone. In some embodiments, the data depicting the face of the subject may be detailed two-dimensional or three-dimensional face image data captured by a photobooth skin analyzer such as a NEXA POS skin analyzer.

In some embodiments, the computing system may present one or more prompts to the subject to guide capture of the data depicting the face of the subject. FIG. 3A-FIG. 3E are non-limiting examples of interfaces that guide a subject through a video capture process according to various aspects of the present disclosure. The interfaces present a series of prompts for the subject to smile, frown, say the letter O, and obtain further image data of various skin areas. In some embodiments, instead of presenting prompts to the subject to guide capture of the data depicting the face of the subject, the data depicting the face of the subject may be automatically collected during a video-based interview with a clinician.

At block 204, the computing system determines features based on the data depicting the face of the subject. In some embodiments, the computing system may use still images from the data (or derived from the data) to measure facial structures (e.g., overall facial shape, cheekbone location, etc.), skin tone, and/or other static facial features. In some embodiments, the computing system may use these still images to measure various clinical signs of aging, including but not limited to the presence and/or size of wrinkles or skin folds, eye bags, spots, and/or other signs of aging. In some embodiments, the computing system may use video imagery from the data to measure facial movements while the face is moving between various poses prompted by the computing system. The measured facial movements may be used as additional features.

In some embodiments, features may also be generated using other types of information. Some examples of visible features include, but are not limited to skin type, phenotype, skin surface quality, skin tone homogeneity, skin glow, facial structure measurements, features calculated from facial expressions/movements, and features calculated from parents' pictures. Some examples of invisible features include, but are not limited to lifestyle information (e.g., smoking, sport participation, time indoors/outdoors, etc.), exposome information (e.g., pollution, time indoors/outdoors, UV exposure, chemical exposure, allergen exposure, etc.), melanin accumulation, skin micro relief, menstrual cycles, -omics information (e.g., proteomics, microbiomics, etc.), skinflammation, and hormone levels.

At block 206, the computing system provides the features to an ageotype classifier to generate a predicted skin ageotype for the subject. Any suitable type or combination of types of classifier may be used as an ageotype classifier, including but not limited to decision trees, naïve Bayes classifiers, k-nearest neighbors classifiers, support vector machines, and artificial neural networks. The classifier may be trained using any suitable technique, including but not limited to determining a set of labeled training data using subjects for which ground truth skin ageotype information is known, and training the classifiers using the labeled training data via a technique including but not limited to gradient descent.

At block 208, the computing system generates the personalized skincare recommendation based on at least the predicted skin ageotype. In some embodiments, the computing system may be configured with information regarding the likely clinical signs of aging to be experienced by subjects of the predicted skin ageotype, and the personalized skincare recommendation may be determined to address these likely clinical signs of aging. In some embodiments, the personalized skincare recommendation may also take other factors into consideration, including but not limited to exposome information (including but not limited to environmental information such as pollution, humidity, temperatures, etc automatically collected through sensor devices or automatically collected from data stores), lifestyle information (including but not limited to sleep quantity or quality information collected using a wearable device), proteomic information, subdepidermal imaging information, and/or other information.

For example, in some embodiments, the computing system may use the facial structure, skin ageotype, and other information to produce a report such as the following:

The subject's objective age is 46.

The subject belongs to the skin inflammaging skin ageotype and has an oval-shaped face with high cheek bones Subjects with these characteristics tend to be prone to dark spots and wrinkles but have minimal sagginess Based on these characteristics and other personal data (such as the exposome, lifestyle, proteomics, subdepidermal imaging, and/or other other data we have collected), the subject's physiological skin age is 42.

To improve the skin age score, the subject should capitalize on their assets of firm, wrinkle free skin by focusing on high SPF, AOX, and a diet rich in fatty acids to reduce and prevent inflammation.

To keep a wrinkle free skin surface and restore a youthful glow, the subject should use a retinol serum with SPF because the subject is a responder to retinol and not vitamin C.

The subject is encouraged to take weekly pictures to track their aging score and to get more personalized advice to adjust their skin routine to continue to prevent inflammaging and to get visible results In some embodiments, the personalized skincare recommendation may be provided in a more complex format. For example, a visualization of the subject may be generated that represents the subject's skin aging trajectory after applying the personalized skincare recommendation, and/or without applying the personalized skincare recommendation. The visualization may include a selfie or video that is generated using suitable machine learning techniques (including but not limited to generative adversarial networks) to show the skin aging trajectory.

In some embodiments, the personalized skincare recommendation may include quantifications of the skin ageotype, skin aging trajectory, and/or physiological skin age. For example, an age clock and/or a photo age clock may be generated to present this information in a graphical format.

In some embodiments, the personalized skincare recommendation may include one or more active ingredients for addressing the predicted clinical signs of aging for the skin ageotype of the subject. In some embodiments, the personalized skincare recommendation may therefore include instructions for formulating a product that includes the one or more active ingredients. In some embodiments, the personalized skincare recommendation may therefore include suggestions of pre-formulated products that include the one or more active ingredients.

Figure 4:
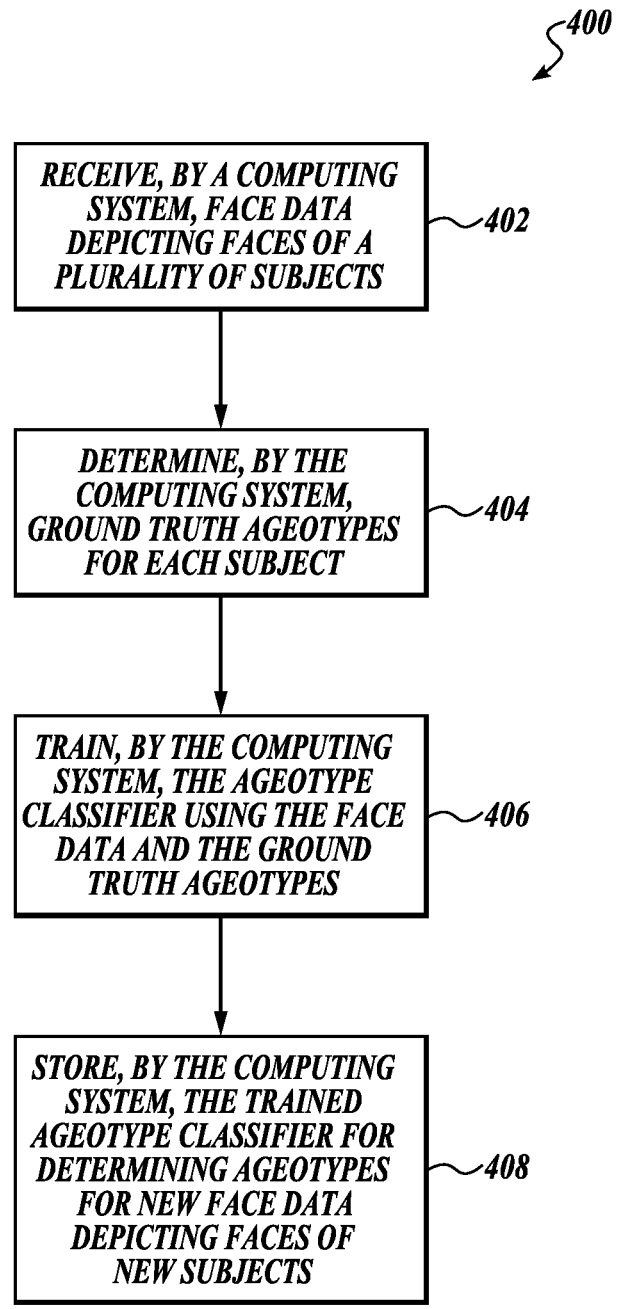
FIG. 4 illustrates a method 400 in accordance with a non-limiting example embodiment of the present disclosure.

FIG. 4 is a flowchart illustrating a non-limiting example embodiment of a method of training an ageotype classifier according to various aspects of the present disclosure.

At block 402, a computing system (such as the skincare personalization computing system 110) receives face data depicting faces of a plurality of subjects. The face data is similar to the face data collected at block 202.

At block 404, the computing system determines ground truth skin ageotypes for each subject. The ground truth skin ageotypes may be determined using any suitable technique. In some embodiments, the ground truth skin ageotypes may be determined based on an evaluation by a trained clinician, and the clinician may input the ground truth skin ageotypes into the computing system.

At block 406, the computing system trains the ageotype classifier using the face data and the ground truth skin ageotypes. In some embodiments, the computing system may generate features as described in block 204, and use the features as input data for training the ageotype classifier. As discussed above, the ageotype classifier may be trained using any suitable technique, including but not limited to gradient descent.

At block 408, the computing system stores the trained ageotype classifier (such as in the data store 108) for determining skin ageotypes for new face data depicting faces of new subjects.

Figure 5:
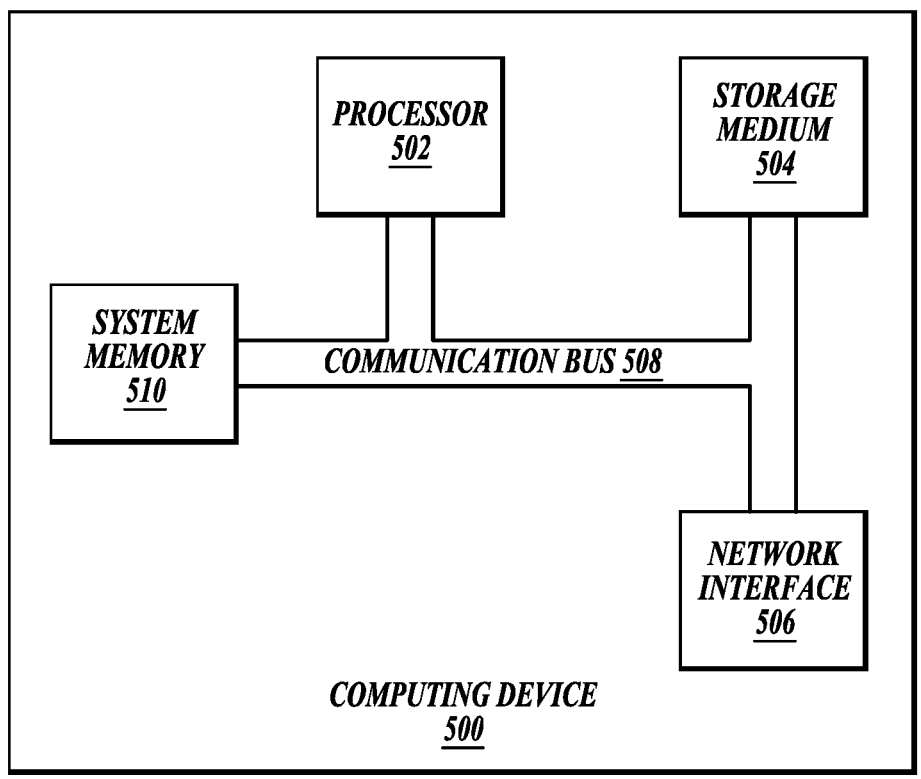
FIG. 5 is a block diagram that illustrates a non-limiting example embodiment of a computing device appropriate for use as a computing device with embodiments of the present disclosure.

FIG. 5 is a block diagram that illustrates aspects of an exemplary computing device 500 appropriate for use as a computing device of the present disclosure. While multiple different types of computing devices were discussed above, the exemplary computing device 500 describes various elements that are common to many different types of computing devices. While FIG. 5 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Some embodiments of a computing device may be implemented in or may include an application-specific integrated circuit (ASIC), a field-programmable gate array (FPGA), or other customized device. Moreover, those of ordinary skill in the art and others will recognize that the computing device 500 may be any one of any number of currently available or yet to be developed devices.

In its most basic configuration, the computing device 500 includes at least one processor 502 and a system memory 510 connected by a communication bus 508. Depending on the exact configuration and type of device, the system memory 510 may be volatile or nonvolatile memory, such as read only memory ("ROM"), random access memory ("RAM"), EEPROM, flash memory, or similar memory technology. Those of ordinary skill in the art and others will recognize that system memory 510 typically stores data and/or program modules that are immediately accessible to and/or currently being operated on by the processor 502. In this regard, the processor 502 may serve as a computational center of the computing device 500 by supporting the execution of instructions.

As further illustrated in FIG. 5, the computing device 500 may include a network interface 506 comprising one or more components for communicating with other devices over a network. Embodiments of the present disclosure may access basic services that utilize the network interface 506 to perform communications using common network protocols. The network interface 506 may also include a wireless network interface configured to communicate via one or more wireless communication protocols, such as Wi-Fi, 2G, 3G, LTE, WiMAX, Bluetooth, Bluetooth low energy, and/or the like. As will be appreciated by one of ordinary skill in the art, the network interface 506 illustrated in FIG. 5 may represent one or more wireless interfaces or physical communication interfaces described and illustrated above with respect to particular components of the computing device 500.

In the exemplary embodiment depicted in FIG. 5, the computing device 500 also includes a storage medium 504. However, services may be accessed using a computing device that does not include means for persisting data to a local storage medium. Therefore, the storage medium 504 depicted in FIG. 5 is represented with a dashed line to indicate that the storage medium 504 is optional. In any event, the storage medium 504 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

Suitable implementations of computing devices that include a processor 502, system memory 510, communication bus 508, storage medium 504, and network interface 506 are known and commercially available. For ease of illustration and because it is not important for an understanding of the claimed subject matter, FIG. 5 does not show some of the typical components of many computing devices. In this regard, the computing device 500 may include input devices, such as a keyboard, keypad, mouse, microphone, touch input device, touch screen, tablet, and/or the like. Such input devices may be coupled to the computing device 500 by wired or wireless connections including RF, infrared, serial, parallel, Bluetooth, Bluetooth low energy, USB, or other suitable connections protocols using wireless or physical connections. Similarly, the computing device 500 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of determining a personalized skincare recommendation, the method comprising:
   receiving, by a computing system, data depicting a face of a subject;
   collecting, by the computing system, at least one of exposome information and primary spoken language information;
   determining, by the computing system, features based on the data depicting the face of the subject;
   providing, by the computing system, the features based on the data depicting the face of the subject and the at least one of the exposome information and the primary spoken language information to an ageotype classifier to generate a predicted ageotype for the subject; and
   generating, by the computing system, the personalized skincare recommendation based on at least the predicted ageotype.

2. The method of claim 1, wherein the features based on the data depicting the face of the subject include one or more of a facial structure, a skin tone, and a facial movement.

3. The method of claim 1, wherein the data depicting the face of a subject is a selfie picture, a selfie video, a three-dimensional scan, or an image obtained by a photo booth skin analyzer.

4. The method of claim 1, further comprising:
   presenting, by the computing system, one or more prompts to guide collection of the data depicting the face of the subject.

5. The method of claim 4, wherein presenting the one or more prompts to guide collection of the data depicting the face of the subject includes one or more of:
   presenting a prompt for the subject to smile;
   presenting a prompt for the subject to frown; and
   presenting a prompt for the subject to say the letter O.

6. The method of claim 4, further comprising:
presenting, by the computing system, one or more prompts to guide collection of close-up images of indicated skin areas of the subject.

7. The method of claim 6, wherein presenting the one or more prompts to guide collection of close up images of indicated skin areas of the subject include one or more of:
presenting a prompt to collect a close up image of a forehead area;
presenting a prompt to collect a close-up image of a cheek area;
presenting a prompt to collect a close-up image of a chin area; and
presenting a prompt to collect a closeup image of a decollete area.

8. The method of claim 1, further comprising determining, by the computing system, a predicted clinical sign of aging based on the predicted ageotype;
wherein generating the personalized skincare recommendation based on at least the predicted ageotype includes generating the personalized skincare recommendation to address the predicted clinical sign of aging.

9. The method of claim 1, wherein the predicted ageotype indicates a presence or absence of inflammaging.

10. A non-transitory computer-readable medium having computer-executable instructions stored thereon that, in response to execution by one or more processors of a computing system, cause the computing system to perform actions comprising:
receiving, by the computing system, data depicting a face of a subject;
collecting, by the computing system, at least one of exposome information and primary spoken language information;
determining, by the computing system, features based on the data depicting the face of the subject;
providing, by the computing system, the features based on the data depicting the face of the subject and the at least one of the exposome information and the primary spoken language information to an ageotype classifier to generate a predicted ageotype for the subject; and
generating, by the computing system, the personalized skincare recommendation based on at least the predicted ageotype.

11. The non-transitory computer-readable medium of claim 10, wherein the features based on the data depicting the face of the subject include one or more of a facial structure, a skin tone, and a facial movement.

12. The non-transitory computer-readable medium of claim 10, wherein the data depicting the face of a subject is a selfie picture, a selfie video, a three-dimensional scan, or an image obtained by a photo booth skin analyzer.

13. The non-transitory computer-readable medium of claim 10, wherein the actions further comprise:
presenting, by the computing system, one or more prompts to guide collection of the data depicting the face of the subject.

14. The non-transitory computer-readable medium of claim 13, wherein presenting the one or more prompts to guide collection of the data depicting the face of the subject includes one or more of:
presenting a prompt for the subject to smile;
presenting a prompt for the subject to frown; and
presenting a prompt for the subject to say the letter O.

15. The non-transitory computer-readable medium of claim 13, wherein the actions further comprise:
presenting, by the computing system, one or more prompts to guide collection of close-up images of indicated skin areas of the subject.

16. The non-transitory computer-readable medium of claim 15, wherein presenting the one or more prompts to guide collection of close up images of indicated skin areas of the subject include one or more of:
presenting a prompt to collect a close up image of a forehead area;
presenting a prompt to collect a close-up image of a cheek area;
presenting a prompt to collect a close-up image of a chin area; and
presenting a prompt to collect a closeup image of a decollete area.

17. The non-transitory computer-readable medium of claim 10, wherein the actions further comprise determining, by the computing system, a predicted clinical sign of aging based on the predicted ageotype;
wherein generating the personalized skincare recommendation based on at least the predicted ageotype includes generating the personalized skincare recommendation to address the predicted clinical sign of aging.

18. The non-transitory computer-readable medium of claim 10, wherein the predicted ageotype indicates a presence or absence of inflammaging.

* * * * *